United States Patent [19]

Lindvay

[11] 4,353,820
[45] Oct. 12, 1982

[54] FLAME-RETARDED HIGH IMPACT POLYSTYRENE COMPOSITION

[76] Inventor: Michael W. Lindvay, 7005 Salge Ct., Ft. Wayne, Ind. 46815

[21] Appl. No.: 83,745

[22] Filed: Oct. 11, 1979

Related U.S. Application Data

[63] Continuation-in-part of Ser. No. 911,642, Jun. 1, 1978, abandoned.

[51] Int. Cl.$^3$ .................... C08L 25/04; C08L 71/04; C08K 3/22
[52] U.S. Cl. ................................ 524/409; 525/68; 525/132; 528/212; 524/408; 524/430; 524/434
[58] Field of Search ................... 525/68, 132; 260/45.75 A, 45.75 B, 45.75 D, 45.75 V

[56] References Cited

U.S. PATENT DOCUMENTS

| 3,671,487 | 6/1972 | Abolins | 260/40 R |
| 4,077,934 | 3/1978 | Lee, Jr. | 260/30.6 R |
| 4,113,797 | 9/1978 | Lee, Jr. | 260/876 B |
| 4,123,474 | 10/1978 | Katchman | 260/874 |
| 4,123,475 | 10/1978 | Abolins et al. | 260/874 |
| 4,129,555 | 12/1978 | White | 260/823 |

OTHER PUBLICATIONS

Vandenberg, Ed. *Polyethers,* (A.C.S. 1975), pp. 169–184, (ACS Symp. Ser. 1974 (6)).
Chem. Abs. 82(22): 140962h; 82(26): 171488n.
Chem. Abs. 89: 44680p.
Lyons, *The Chem. & Uses of Fire Retardants,* (Wiley 1970), pp. 20, 21.

*Primary Examiner*—Carman J. Seccuro

[57] ABSTRACT

A flame-retarded polystyrene composition which does not bloom comprising at least about 50 percent (by combined weight of polystyrene, poly[brominated phenylene oxide], and enhancing agent) of high impact polystyrene, from about 9 to about 22 percent (by weight) of poly(brominated phenylene oxide), and from 1 to about 10 percent (by weight) of enhancing agent is disclosed.

5 Claims, No Drawings

FLAME-RETARDED HIGH IMPACT POLYSTYRENE COMPOSITION

This is a continuation-in-part of the copending application Ser. No. 911,642, filed June 1, 1978, now abandoned.

FIELD OF THE INVENTION

A non-blooming flame-retarded high impact polystyrene composition which contains up to about 10 percent (by weight) of an enhancing agent and up to about 22 percent (by weight) of a polymeric product derived from a brominated phenol.

DESCRIPTION OF THE PRIOR ART

Polystyrene is an extraordinarily versatile thermoplastic which may be used in, e.g., low density insulation foams, molded parts, extended and formed sheets for containers and appliances, high density foamed parts, formed dinnerware, etc. High impact polystyrene is especially valuable for usage in appliances where good impact-resistant properties are required; and a substantial amount of high impact polystyrene is used to produce television cabinets.

The Underwriters' Laboratory of Chicago, Ill. has promulgated a flammability standard for television cabinets containing high impact polystyrene: samples of said polystyrene must obtain either a V-0 or V-1 rating when tested in accordance with test U.L. 94 in order to meet this standard. Notwithstanding its unique properties, high impact polystyrene cannot be used in these television cabinets unless it possesses the requisite degree of nonflammability.

Poly(phenylene oxide) compositions are well known in the art; and they are extensively described in the literature. See, e.g., Journal of the American Chemical Society, 1921 (43), pp. 131–159 (reactions of certain brominated phenol salts); Nippon Kagaku Kaishi, 1976 (10), pp. 1608–1614 (polymerization of sodium 2,4,6-tribromophenolate); Journal of the American Chemical Society, 1960 (82), 3632–3634 (polymerization of the silver salt of 2,4,6-tribromphenol by iodine); and the like. There are many prior art references, both domestic and foreign, which describe these compositions.

Poly(phenylene oxide) compositions appear to be incompatible with most polymers. Thus, e.g., they are incompatible with polycarbonates, polysulfones, butadiene-acrylonitrile copolymers, epichlorohydrin-ethylene oxide copolymers, methyl vinyl ether-maleic anhydride copolymers, polyester-urethane, styrene-acrylonitrile copolymers, styrene-methylmethacrylate copolymers, vinyl chloride-vinyl acetate copolymers, and the like; see, for example, an article by Krause entitled "Polymer Compatibility" appearing in the Journal of Macromolecular Science—Reviews of Macromolecular Chemistry, C7(2), 251–314 (1972).

Blends of polystyrene and poly(phenylene oxide) are well known to the art; U.S. Pat. No. 3,383,435 describes and claims the. These blends, however, are flammable. Thus, e.g., U.S. Pat. No. 3,663,654 discloses that "the admixture of a polyphenylene ether with a styrene resin destroys flame retardant properties"; Example 4 of this patent teaches that a blend of 20 parts of poly(2,6-dimethyl-1,4-phenylene ether), 80 parts of high impact polystyrene, and 1 part of red phosphorus" ... is incapable of passing the Underwriters' Laboratory test ... " described in Underwriters' Laboratories in its Bulletin No. 94. Thus, e.g., U.S. Pat. No. 3,639,506 discloses that " ... many blends comprising a styrene resin, even in low concentration, with a polyphenylene ether have poor flame retardant properties and are unable to meet the requirements established by various testing laboratories such as the Underwriters' Laboratories"; Example 1 of this patent teaches that a blend containing 55 parts of poly(2,6-dimethyl-1,4-phenylene ether) and 45 parts of high impact polystyrene, after being molded into test bars and tested for flammability, " ... burned completely and dripped after ignition thereof." Thus, e.g., U.S. Pat. No. 3,883,613 teaches that "the styrene resin component causes the compositions to be normally flammable, because styrene resins burn at a slow rate upon ignition, and they drip flamming resin."

It is undesirable to have a high impact polystyrene whose flame retardant exudes to the surface after the polystyrene has been formed into a television cabinet. This phenomenon, known as blooming, has several very adverse affects: it produces aesthetically objectionable effects, it contaminates liquids and other products in contact with the polystyrene, and it decreases the concentration of the flame retardant in the polystyrene.

There does not appear to be much literature which attempts to describe the mechanism(s) of blooming. It is suspected that this is so because blooming is an enigmatic and unpredictable phenomenon.

In most plastics, a high concentration of an additive in the plastic increases the likelihood of blooming occurring. However, in polyvinyl chloride compositions, blooming is more likely to occur at the low additive concentrations. See, e.g., pp. 133–134 of "Vinyl and Applied Polymers", Vol. 2 (CRC Press, Cleveland, Ohio, 1971).

Blooming will occur if the additive is not "compatible" with the polymer matrix. Thus, e.g., the prior art discloses that "bleeding and blooming phenomena are obviously related to the kinetics of diffusion and consequently are dependent upon parameters such as compatibility of the additive with the polymer, molecular size of the additive, physicochemical interactions between additive and polymer molecules, configuration of polymer chains and intermolecular voids, etc." Mascia, "The Role of Additives in Plastics", (John Wiley & Sons, New York, 1974) p. 6.

The "Encyclopedia of Polymer Science and Technology", Vol. 2 (Interscience, New York, 1965) teaches that "bloom is a visible exudation (or efflorescence) caused by lubricant, plasticizer, etc. on the surface of a polymer (1). It is usually the result of incompatibility of the additive with the polymer or of exclusion of additive or low-molecular-weight polymer upon the onset of crystallization of the polymer." (at p. 531)

If the theory that incompatability of an additive with the polymer matrix causes blooming is correct, then it would help explain why so many flame retardant additives bloom in thermoplastic systems: very few of them are truly compatible with the polymer matrices. In an article appearing at pages III-211 to III-213 of the "Polymer Handbook", Second Edition (John Wiley & Sons, New York, 1975), L. Bohn states that "compatibility ... will refer to the miscibility on an intimate polymer scale of polymers in the solid state. Such miscibility will only take place if the Gibbs free energy of mixing ... is negative. The entropy term ... is unsignificant in the mixing of high molecular weight species. The enthalphy of mixing ... is normally positive to such an extent as to overcompensate for the entropy term, resulting generally in an unfavorable energy of mixing for polymer blends. Real compatibility is therefore a rare event, especially in the solid state."

Poly(phenylene oxide) compositions possess excellent flammability properties, generally being self-extinguishing. However, those skilled in the art do not appear to have attempted to utilize them to prepare flame-retarded, non-blooming high impact polystyrene compositions comprised of a minor portion of poly (phenylene oxide). This may be the case because the poly(phenylene oxides) are polymeric in nature, incompatible with other polymers, and, according to the art, should bloom; or it may be the case because the art teaches that blends of polystyrene and poly(phenylene oxide)s are flammable.

Applicant has discovered that, unexpectedly, a particular three-component blend which contains at least 50 percent (by weight) of high impact polystyrene, at least 9 percent (by weight) of a particular poly(brominated phenylene oxide), and an enhancing agent is non-blooming, is flame-retarded, and possesses excellent physical properties.

SUMMARY OF THE INVENTION

In accordance with this invention, there is provided a non-blooming flame-retarded composition comprised of at least about 50 percent (by combined weight of polystyrene, poly[brominated phenylene oxide], and enhancing agent) of high impact polystyrene, from about 9 to about 22 percent (by weight) of poly(brominated phenylene oxide), and from about 1 to about 10 percent (by weight) of enhancing agent, wherein: (a) said poly(brominated phenylene oxide) is a condensation product derived from a brominated phenol selected from the group consisting of tribromophenol, tetrabromophenol, and pentabromophenol; (b) said condensation product has a repeating structural unit of the formula

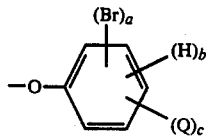

wherein a is an integer of from about 1 to about 4, b is an integer of from about 0 to about 2, c is an integer of from about 1 to about 5, a plus b plus c equal 5, Q is a monovalent bond from a carbon atom in the aromatic nucleus of said repeating structural unit to an oxygen atom bonded to an aromatic nucleus, and the polymeric units containing said repeating structural units comprise at least 80 percent (by weight) of said poly(brominated phenylene oxide) condensation product; (c) said poly(brominated phenylene oxide) condensation product contains from about 17 to about 31 percent (by weight) of elemental carbon, from about 0 to about 1.0 percent (by weight) of elemental hydrogen, from about 3 to about 8 percent (by weight) of elemental oxygen, and at least 60 percent (by weight) of elemental bromine; and (d) said condensation product has a molecular weight of at least about 750, and one or more polymeric units containing at least four aromatic nuclei per unit comprise at least about 80 percent (by weight) of said product.

PREFERRED EMBODIMENTS

The flame-retarded composition of this invention contains at least about 50 percent (by combined weight of polystyrene, poly[brominated phenylene oxide], and enhancing agent) of high impact polystyrene. It is preferred that the flame-retarded composition of this invention contain at least 65 percent (by combined weight) of high impact polystyrene.

Any of the high impact polystyrenes known in the art may be used in the compositions of this invention. Many of these are rubber modified; elastomer is dispersed in the polystyrene in the form of discrete particles. Many of these are produced by polymerizing styrene in the presence of an elastomeric composition. One such composition is made by dissolving poly(butadiene-costyrene) in styrene and polymerizing the solution by methods well known to the art. Often the elastomer used in these polystyrenes is a butadiene homopolymer or copolymer with a glass transition temperature below about 50 degrees centigrade. These high impact polystyrenes typically have notched Izod impact strengths of from about 0.7 to about 3.5 foot-pounds per inch of notch (ASTM D256-73, one-half inch bar), tensile strengths of from about 1,900 to about 4,000 pounds per square inch (ASTM D638-76), tensile moduli of from about 200,000 to about 430,000 pounds per square inch (ASTM D638-76), elongations of from about 10 to about 75 percent (ASTM D638-76), flexural strengths of from about 5,500 to about 12,500 pounds per square inch (ASTM D790-71), and unannealed heat distortion temperatures of from about 150 to about 205 degrees Fahrenheit (ASTM D648, 264 pounds/square inch).

The high impact polystyrene composition used in the flame-retarded compositions of this invention contains polymer units derived from the compound of the formula

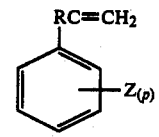

wherein R is hydrogen, lower alkyl, or halogen; Z is a member selected from the class consisting of vinyl, hydrogen, chlorine, and lower alkyl; and p is a whole number equal to from 0 to 5; said polymer units comprise at least 25 percent (by weight) of the high impact polystyrene composition. The high impact polystyrene may be comprised of homopolymers such as, e.g., polystyrene and polychlorostyrene. It may be comprised of rubber modified polystyrene. It may be comprised of styrene-containing copolymers such as styreneacrylonitrile copolymers (SAN), styrenebutadiene copolymers, styrene-acrylonitrile-α-alkyl styrene copolymers, poly-α-methylstyrene, copolymers of ethylvinyl benzene and divinylbenzene, and the like.

The flame-retarded polystyrene compositions of this invention contain from about 1 to about 10 percent (by combined weight of polystyrene, poly[brominated phenylene oxide], and enhancing agent) of enhancing agent and from about 9 to about 22 percent (by combined weight) of poly(brominated phenylene oxide) condensation product which is derived from brominated phenol; this condensation product has a repeating structural unit of the formula

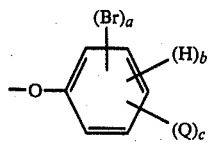

wherein a is an integer of from about 1 to about 4, b is an integer of from about 0 to about 2, c is an integer of from about 1 to about 5, a plus b plus c equal 5, and Q is a monovalent bond from a carbon atom in the aromatic nucleus of said repeating structural unit to an oxygen bonded to an aromatic nucleus. This monovalent bond may exist any place on the aromatic nuclei in the composition wherein there was a carbon-bromine bond; it is formed by the diplacement of bromine. Thus, for example, it may exist in the position para to the oxygen-carbon bond. One repeating structural unit which has this para bond may be represented by the formula

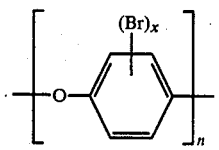

wherein x is 2,3, or 4 (and preferably is 2 or 3); this repeating unit forms linear chains. Thus, in other instances where c is 1, the monovalent bond may exist at the ortho position (hereinafter referred to as "II"). The bond may exist at both the ortho and para positions when c is 2 (hereinafter referred to as "III"); and it may exist ortho, ortho, and para to the carbon-oxygen bond when c is 3 (hereinafter referred to as "IV"). The poly(bromophenylene oxide) condensation product contains at least one of the repeating structural units denoted I, II, III, and IV. At least 80 percent (by weight) of this product is comprised of polymer chains containing one or more of these units.

The poly(brominated phenylene oxide) product has a molecular weight of at least about 750. The molecular weight of this product may be determined by the vapor phase osmometry method described in ASTM test D2503-67. It is preferred, however, to determine the molecular weight of this product by the gel permeation chromatography method known to the art; and, unless otherwise specified, references to molecular weight in this specification refer to number-average molecular-weights determined in accordance with the gel permeation method with polystyrene reference standards.

In the gel permeation method used to ascertain the molecular weights of the poly(brominated pheylene oxide) compositions described in this specification, four Waters Associates, Inc. stainless stell columns packed with Styragel ® are connected in series; these columns, each of which measures 48" long × 0.375" in diameter, have pore sizes of 15,000–50,000 angstroms, 8,000 angstroms, 250 angstroms, and 250 angstroms, respectively. The solvent utilized is tetrahydrofuran; 33.5 milligrams of the poly(brominated phenylene oxide) sample are mixed with 15.0 milliliters of tetrahydrofuran, and the mixture is introduced into the chromatograph. A flow rate of 1 milliliter of tetrahydrofuran per minute is used. The chromatograph is calibrated with commercially available polystyrene standards, and the molecular weight values found are reported in terms of polystyrene.

It is preferred that the number average molecular weight of the poly(brominated phenylene oxide) compositions of this invention be less than about 100,000.

The poly(brominated phenylene oxide) condensation product is derived from a brominated phenol selected from the group consisting of tribromophenol, tetrabromophenol, and pentabromophenol. It is preferred that the brominated phenol be selected from the group consisting of tribromophenol and tetrabromophenol; and it is most preferred that the brominated phenol be tribromophenol.

The poly(brominated phenylene oxide) condensation product contains from about 17 to about 31 percent (by weight) of carbon, from about 0 to about 1.0 percent (by weight) of elemental hydrogen, from about 3 to about 8 percent (by weight) of elemental oxygen, and at least about 60 percent (by weight) of elemental bromine. It is preferred that this product contain from about 62 to about 66 percent (by weight) of elemental bromine.

It is preferred that the poly(brominated phenylene oxide) product used in the composition of this invention, when fused to form test specimens 0.125" thick, have a notched Izod impact strength of less than about 0.5 foot-pounds per inch of notch (ASTM D256), an elongation of less than about 2.0 percent, and a tensile strength of less than about 200 pounds per square inch (ASTM D638).

The poly(brominated phenylene oxide) product may be prepared by any of several methods well known to those skilled in the art. Generally, the brominated phenol is contacted with an effective amount of activating agent and allowed to condense for a period of up to 48 hours at a temperature of up to about 300 degrees centigrade. Suitable activating agents include, without limitation, heat, light, organic and inorganic peroxides such as benzoyl peroxide, hydrogen peroxide, dimethane sulfonyl peroxide, lauroyl peroxide, caprylyl peroxide, succinic peroxide, acetyl peroxide, p-tertiarybutyl benzoyl peroxide, tertiary-butylperoxy isopropyl carbonate peroxide, hydroxyheptyl peroxide, cyclohexane peroxide, 2,5-dimethylhexane peroxide, di-tertiarybutyl diperphthalate peroxide, tertiary butyl perbenzoate peroxide, and the like; azo compounds, such as azobisisobutyronitrile, for example; persulfates, such as ammonium persulfate, potassium persulfate, and sodium persulfate; hypochlorites; ferricyanides; ferric chloride; copper salts wherein the copper has a valency of one or two such as, e.g. cuprous-2,4,6-tribromophenate, cupric-2,4,6-tribromophenate, cuprous chloride, cupric chloride, cuprous nitrate, cupric nitrate, cuprous sulfate, cupric sulfate, mixtures of one or more of the aforementioned salts, etc.; metal oxides, such as lead oxide, mercury oxide, silver oxide, and the like; halogen, such as iodine, bromine, and chlorine; lead tetracetate; sodium bismuthate; etc. Generally, any of the activators known to promote free radical chain initiation may be used.

Alternatively, one may use a metal salt of the brominated phenol with the activating agents. Suitable salts which may be utilized include, without limitation, the lithium, sodium, potassium, barium, zinc, and tin salts of the brominated phenol. Other phenolates well known to those skilled in the art may also be used.

The brominated phenol (or the metallic salt derived from it) may be contacted with the activating agent in the solid state. Alternatively, one may conduct the polymerization of the brominated phenol (or its salt) in a suitable inert solvent. In general, any of the inert aqueous or organic solvents in which phenol or its salt are known to be soluble may be used to prepare the flame retarding condensation product. Suitable solvents include, without limitation, water, dimethylsulfoxide, acetone, hexane, methanol, ethanol, propanol, butanol, benzene, toluene, tetrahydrofuran, etc. Aqueous salt solutions wherein the salt is selected from the group consisting of barium chloride, calcium chloride, magnesium chloride, strontium chloride, potassium chloride, lithium chloride, sodium chloride, and the like may also be utilized. Mixtures of organic solvents and water may be used; thus aqueous acetone solutions, benzene and water, aqueous alkaline solutions and organic compounds insoluble in water (such as octyl alcohol, toluene, and heptane), carbon tetrachloride and water, amyl alcohol and water, and the like are suitable.

One of many methods which may be used to prepare this product involves dissolving a metal hydroxide in water and, to the solution thus formed, adding activating agent and the brominated phenol; thereafter the reaction mixture is maintained at a specified temperature.

In this method, an emulsifying agent may be used to suspend the condensation product in aqueous media; when so used, from about 0.1 to about 5.0 percent of it (by weight of water in the hydroxide solution) should be present in the reaction mixture.

In this method, an alkali or alkaline earth metal hydroxide may be used. It is preferred to use a metal hydroxide selected from the group consisting of sodium hydroxide, potassium hydroxide, and lithium hydroxide; sodium hydroxide is the most preferred. From about 0.5 to about 5.0 moles of the hydroxide per liter of water is utilized. It is preferred to use from about 1 to about 3 moles of hydroxide per liter of water; it is most preferred to use about 2 moles of the hydroxide per liter of water.

The brominated phenol described hereinabove is added to the reaction mixture at a concentration of from about 0.5 to about 5 moles per liter of water to make up the hydroxide solution in this method. It is preferred to use from about 1 to about 3 moles of phenol per liter of water. It is most preferred that the concentration be about 2 moles of phenol per liter of water.

In this method, although it is not essential, organic solvent may be added to the reaction mixture; any of the organic solvents listed hereinabove may be utilized. When organic solvent is used, it is preferred that from 1 to about 20 percent of it (by volume of water used to make up the hydroxide solution) be utilized. It is more preferred to use from about 3 to about 10 percent of organic solvent in this process; and it is most preferred to use from about 4 to about 8 percent of organic solvent. Some of the preferred organic solvents include toluene, benzene, chloroform, chlorinated benzenes, and the like.

Activating agent is contacted with the reaction mixture after all of the other components are present in this process. When the activating agent is solid, liquid, or gaseous, at least about $1 \times 10^{-5}$ moles of it (based upon liters of water used to make up the hydroxide solution) is used; it is preferred to use from about 0.01 to about 0.1 moles of these activating agents.

After the activating agent has been contacted with the reaction mixture, the reaction mixture is maintained at a temperature of from about 20 to about 180 degrees centigrade for from about 5 to about 300 minutes in this process. It is preferred to maintain the reaction mixture at a temperature of from about 20 to about 100 degrees centigrade for from about 15 to about 120 minutes. It is most preferred to maintain the reaction mixture at a temperature of from about 45 to about 65 degrees centigrade for from about 20 to about 40 minutes.

In this process, it is preferred that the reaction be run at a pressure of from about 1.0 to about 20 atmospheres. It is more preferred to use a pressure of about 1.0 atmosphere during the reaction.

The flame-retarded polystyrene composition of this invention contains from about 1 to about 10 percent (by combined weight of polystyrene, poly[brominated phenylene oxide], and enhancing agent) of enhancing agent. The enhancing agents known in the art may be used in the compositions of this invention; some of these are, e.g., the oxides and halides of the metals of groups IVA and VA of the Periodic Table such as the oxides and halides of antimony, bismuth, arsenic, tin, lead, and germanium; antimony oxychloride, antimony chloride, antimony oxide, stannic oxide, stannic chloride, arsenous oxide, arsenous chloride, and the like. Other enhancing agents well known to those skilled in the art are the organic and inorganic compounds of phosphorous, nitrogen, boron, and sulfur; thus, e.g., triphenyl phosphate, ammonium phosphate, zinc borate, thiourea, urea, stannic sulfide, and the like are suitable enhancing agents. The oxides and halides of titanium, vanadium, chromium, magnesium are also used as enhancing agents as are the hydrates of these compounds; thus, e.g., titanium dioxide, titanium chloride, vanadium pentoxide, chromic bromide, manganous oxide, molybdenum trioxide, ammonium molybdate, stannous oxide hydrate, lead hydrate, and combinations thereof may be used. Many antimony compounds, both organic and inorganic, are useful as enhancing agents; antimony sulfide, sodium antimonite, potassium antimonite, antimony butyrate, antimony valerate, antimony caproate, antimony heptylate, antimony caprylate, antimony pelargonate, antimony caprate, antimony cinnamate, antimony anisate, tris(n-octyl) antimonite, tris(2-ethylhexyl) antimonite, tribenzyl antimonite, trimethylolpropane antimonite, pentaerythritol antimonite, glycerol antimonite, and compounds which on decomposition (as by ignition) yield antimony oxide are well known to the art as enhancing agents.

The preferred enhancing agents are the oxides of antimony, arsenic, and bismuth. The more preferred enhancing agents are the oxides of antimony. The most preferred enhancing agent is antimony trioxide.

It is also within the scope of the present invention to employ other materials in the polystyrene compositions of the invention where one so desires to achieve a particular end result. Such materials include, without limitation, adhesion promotors; antioxidants; antistatic agents; antimicrobial agents; colorants; other flame retardants (in addition to the flame retarding condensation product described herein); heat stabilizers; light stabilizers; fillers; reinforcing agents; and other materials well known to those skilled in the art which have been or could be used with polystyrene compositions and which are described, e.g., in Modern Plastics Encyclopedia, Vol. 52, No. 10A, McGraw-Hill, Inc., New York, N.Y. (1975). Said encyclopedia is hereby incorporated in toto by reference into this disclosure.

The above described materials which may be employed in the polystyrene compositions of this invention can be utilized in any amounts which will not substantially adversely affect the properties of these compositions. Thus, the amount used can be zero (0) percent, based on the total weight of the composition, up to that percent at which the composition can still be classified as a plastic. In general, such amount will be from about 0% to about 80%.

The flame retardant additive utilized in the polystyrene composition of this invention contains poly(brominated phenylene oxide) and enhancing agent. Poly(brominated phenylene oxide) comprises at least about 50 percent (by combined weight of poly[brominated phenylene oxide] and enhancing agent) of the flame retardant additive. It is preferred that poly(brominated phenylene oxide) comprise at least 70 percent (by combined weight of poly[brominated phenylene oxide] and enhancing agent) of this additive.

The following examples are provided for the purpose of further illustration only and are not intended to be limitative of the invention disclosed. Unless otherwise specified, all parts are by weight, all weights are in grams, all temperatures are in degrees centigrade, and all volumes are in milliliters.

PREPARATION OF THE FLAME RETARDING CONDENSATION PRODUCTS

Example I

Two hundred milliliters of chloroform were added to a one liter, three-necked, round-bottomed flask fitted with mechanical stirring, addition funnel, reflux condenser, and nitrogen flush. Sixteen and one-half grams of 2,4,6-tribromophenol were added to the chloroform. Thereafter, 2.8 grams of potassium hydroxide were dissolved in 100 milliliters of water, and this solution was then added to the reaction mixture. An aqueous solution of potassium ferricyanide was prepared; 1.6 grams of the potassium ferricyanide were dissolved in 100 milliliters of water. This solution was added over a period of one hour to the reaction mixture. Thereafter, the reaction mixture was maintained at ambient temperature and stirred for 4.5 hours. Then the reaction mixture was poured into a separatory funnel. The bottom chloroform phase was dropped directly into vigorously stirred methanol. The white precipitate which formed was filtered and dried. This product softened at a temperature of from about 220 to about 240 degrees centigrade. It had an intrinsic viscosity (in chloroform, at 25 degrees centigrade) of 0.050 deciliters per gram.

Example II

To a one liter, three-necked, round-bottomed flask fitted with mechanical stirring, reflux condenser, and nitrogen flush were added 100 milliliters of 1,2,4-trichlorobenzene. Thereafter, 58.7 grams of pentabromophenol were added with stirring; and then 2.9 grams of benzoyl peroxide were added to the reaction mixture. A solution of potassium hydroxide (6.8 grams of KOH in 100 milliliters of water) was prepared; and this solution was quickly added to the reaction mixture. Two milliliters of dimethyl sulfoxide and four milliliters of dimethyl formamide were then added to the reaction mixture, causing a mild exotherm. Stirring was continued at ambient temperature for five hours. The reaction mixture was then poured into a separatory funnel. The 1,2,4-trichlorobenzene layer (bottom) was then dropped directly into vigorously stirred acetone. The precipitated product was dissolved in 100 milliliters of tetrahydrofuran and reprecipitated in 450 milliliters of acetone. The product had a softening point of about 290 degrees centigrade.

Examples III–VI

These experiments were conducted in substantial accordance with the procedure described in Example I, but different catalysts and/or different brominated phenols (or mixtures thereof) were used. The results of these experiments are summarized in Table I, below. In Examples III and IV, 2,4,6-tribromophenol was utilized as the reactant. Examples V and VI utilized pentabromophenol.

TABLE I

| EXAMPLE NUMBER | CATALYST (10 MOLE %) | POLYMER YIELD (%) | SOFTENING POINT (°C.) | INTRINSIC VISCOSITY (25° C., chloroform, deciliters/gram) |
|---|---|---|---|---|
| III | K₃Fe(CN)₆ | 80 | 240–260 | 0.050 |
| IV | BENZOYL PEROXIDE | 100 | 225–250 | 0.050 |
| V | K₃Fe(CN)₆ | 10 | 290 | 0.0 |
| VI | BENZOYL PEROXIDE | 86 | 290 | 0.0 |

Examples VII and VIII

The procedure described in Example I was substantially followed with the exception that equimolar amounts of 2,4,6-tribromophenol and pentabromophenol were utilized as the reactant. In Example VII, potassium ferricyanide was utilized as the catalyst (10 mole %); a 12 percent yield of a product with a softening point of from about 210 to about 220 degrees centigrade was obtained. In Example VIII, benzoyl peroxide was utilized as a catalyst (10 mole %); a 98 percent yield of a product with a softening point of 250 degrees centigrade and an intrinsic viscosity (at 25 degrees centigrade in chloroform) of 0.032 deciliters per gram was obtained.

Example IX

Two thousand milliliters of water, 164 grams of sodium hydroxide, 10.7 grams of "Emulsifier 334" (an aryl polyether emulsifier sold by the Milliken Chemical Corporation), 0.7 grams of dodecyl sodium sulfate, and 1324 grams of 2,4,6-tribromophenol were charged to a five-liter flask fitted with mechanical stirring, a thermometer, and a reflux condenser. The reaction mixture was first heated to 100 degrees centigrade and maintained at that temperature for one minute; then it was cooled to a temperature of 33 degrees centigrade. To this mixture was charged 133 milliliters of toluene and 20 grams of benzoyl peroxide. An exothermic reaction occurred, and the reaction temperature was then maintained at 55 degrees centigrade for 0.5 hours. Thereafter, 25 grams of sodium hydroxide were added to the reaction mixture. The reaction mixture was then filtered, the filter cake was washed with 15 liters of water, and the filter cake was dried to give 932 grams of product.

Examples X–XXIII

In substantial accordance with the procedure described in Example IX, poly(brominated phenylene oxide) compositions with different softening point ranges and molecular weights were prepared. The molecular weights of these products were determined in accordance with two different methods: the vapor phase osmometry method described in test ASTM D2503-67, and the gel permeation chromatography test described in this specification wherein polystyrene was used as a reference. The results obtained in the former test are referred to as "V.P.O. Molecular Weight". Three results were obtained in the latter test and are expressed as "$M_w$" (weight average molecular weight), "$M_n$" (number average molecular weight), and "H.I." (the "heterogeneity index" which is calculated by dividing the weight average molecular weight by the number average molecular weight). The results of these experiments are summarized in Table II.

TABLE II

| EXAMPLE NUMBER | SOFTENING POINT RANGE, DEGREES C. | V.P.O. MOLECULAR WEIGHT | $M_n$ | $M_w$ | H.I. |
|---|---|---|---|---|---|
| X | 210–225 | 8370 | 3531 | 8319 | 2.36 |
| XI | 210–230 | >10,000 | 4542 | 8622 | 1.90 |
| XII | 188–200 | 3540 | 2741 | 4549 | 1.66 |
| XIII | 225–240 | >10,000 | 7395 | 12340 | 1.67 |
| XIV | 225–250 | INSOLUBLE | | | |
| XV | 160–175 | 1735 | 2489 | 3630 | 1.46 |
| XVI | 210–227 | >10,000 | 4287 | 9387 | 2.19 |
| XVII | 205–220 | 3295 | 3277 | 6610 | 2.02 |
| XVIII | 205–220 | 3735 | 3510 | 7150 | 2.04 |
| XIX | 205–220 | 4670 | 3832 | 8125 | 2.12 |
| XX | 160–180 | 1875 | 2833 | 4028 | 1.42 |
| XXI | 190–205 | 2480 | 2837 | 5327 | 1.88 |
| XXII | 190–210 | 3855 | 3302 | 4460 | 1.35 |
| XXIII | 200–215 | 3200 | 3189 | 5733 | 1.80 |

FLAME RETARDED POLYSTYRENE COMPOSITIONS

Examples XXIV–XXVII

High impact polystyrene plastic compositions were prepared by incorporating one of the flame retardants described in Examples X through XXIII and antimony trioxide into "Cosden Polystyrene 825 TVP1", a high impact polystyrene available from the Cosden Oil and Chemical Company. These additives were admixed with the polystyrene by addition to a Brabender Prep Center Mixer ("Measuring Head", Model R6, C. W. Brabender Instruments, Inc., South Hackensack, N.J.); the mixer was equipped with a pair of roller-type blades positioned with a head provided with heat transfer means. The resultant mixtures were heated to a temperature of about 205 degrees centigrade; at this temperature they were in a molten state. Each formulation was discharged from the mixer, cooled, and ground into chips. The chips were injection molded in a one-ounce Newbury Injection Molder (Model HI-30 RS, Newbury Industries, Inc., Newbury, Ohio); a 60 second molding cycle with a ram pressure of 2000 p.s.i. was utilized; these chips were subjected to heat, melted, and then injected into a mold in order to provide solid samples for testing.

The samples prepared in Examples XXIV–XXVII contained 15 percent (by weight of total composition) of one of the flame retardants prepared in Examples X–XXIII, 3 percent (by weight of total composition) of antimony trioxide, and 6 percent (by weight of total composition) of "Solprene 411P" (a styrene-butadiene copolymer useful as an impact modifier which is available from the Phillips Petroleum Company). The injection molded samples were tested for Izod impact and heat distortion temperature (unannealed). They were also tested for flammability in accordance with Underwriters' Laboratory Subject No. 94 test (U.L. Tests for Flammability of Plastic Materials, U.L. 94, Feb. 1, 1974). In this test, the test specimen was supported from the upper end, with the longest dimension vertical, by a clamp on a ring stand so that the lower end of the specimen was ⅜" above the top of the burner tube. The burner was then placed remote from the sample, ignited, and adjusted to produce a blue flame ⅜" in height. The test flame was placed centrally under the lower end of the test specimen and allowed to remain for 10 seconds. The test flame was then withdrawn, and the duration of flaming or glowing combustion of the specimen was noted. If flaming or glowing combustion of the specimen ceased within 30 seconds after removal of the test flame, the test flame was again placed under the specimen for 10 seconds immediately after flaming or glowing combustion of the specimen stopped. The test flame was again withdrawn, and the duration of flaming or glowing combustion of the specimen was noted. If the specimen dripped flaming particles or droplets while burning in this test, these drippings were allowed to fall onto a horizontal layer of cotton fibers (untreated surgical cotton) placed one foot below the test specimen. Significantly flaming particles were considered to be those capable of igniting the cotton fibers. The duration of flaming or glowing combustion of vertical specimens after application of the test flame (average of 5 specimens with 10 flame applications) should not exceed 25 seconds (maximum not more than 30 seconds) and the portion of the specimen outside the clamp should not be completely burned in the test.

Materials which complied with the above requirements and did not drip any flaming particles or droplets during the burning test were classified as "V-1". Materials which complied with the above requirement but dripped flaming particles or droplets which burned briefly during the test were classified as "V-2". A "V-0" rating was given to materials wherein the duration of flaming or glowing combustion averaged less than 5 seconds under the conditions specified above.

The results of these experiments are summarized in Table III.

TABLE III

| EXAMPLE NUMBER | PRIOR EXAMPLE DESCRIBING FLAME RETARDANT USED | IZOD IMPACT, FOOT-POUNDS PER INCH (NOTCH) | HEAT DISTORTION TEMPERATURE (UNANNEALED) DEGREES F. | U.L. 94, ⅛" | U.L. 94, 1/16" |
|---|---|---|---|---|---|
| XXIV | XII | 1.32 | 163 | V-0 | V-0 |
| XXV | X | 1.55 | 166 | V-0 | V-0 |
| XXVI | XV | 1.34 | 154 | V-0 | V-0 |
| XXVII | XVI | 1.50 | 161 | V-0 | V-1 |

Examples XXVIII and XXIX

In substantial accordance with the procedure described in Examples XXIV through XXVII, high impact polystyrene composition containing 13 percent (by weight) of the flame retardant of Example X and Shell 335 high impact polystyrene were prepared and evaluated. The composition of Example XXVIII contained 13.0 percent of said flame retardant, 2.6 percent of antimony trioxide, and 6.0 percent of Solprene 411P. The composition of Example XXIX contained 13.0 percent of said flame retardant, 3.25 percent of antimony trioxide, and 6.0 percent of said Solprene 411P Samples prepared from the former composition were evaluated and found to have a U.L. 94⅛" rating of V-0, a notched Izod impact of 1.63 foot-pounds per inch, a Gardner impact of 70, and an unannealed heat distortion temperature of 164 degrees Fahrenheit. Samples prepared from the latter composition were evaluated and found to have a U.L. 94 ⅛" rating of V-0, a notched Izod impact of 1.65 foot-pounds per inch, a Gardner impact of 60, and unannealed heat distortion temperature of 165 degrees Fahrenheit.

Examples XXX-XXXI

The procedure of Examples XXIV through XXIX was repeated with the exception that Dow Styron 492 high impact polystyrene (available from the Dow Chemical Company of Midland, Mich.) was used.

In Examples XXX and XXXI, the flame retardant described in Example XV was used. The average Izod impact was 1.48 foot-pounds per inch, and the heat distortion temperature was 159 degrees Fahrenheit. The U.L. 94⅛" flammability ratings were V-0.

Examples XXXII

The procedure described in Examples XXX-XXXI was followed with the exception that the flame retardant of Example XII was used. The Izod impact was 1.60 foot pounds per inch, the heat distortion temperature was 161 degrees Fahrenheit, the U.L. 94⅛" flammability rating was V-0 and the U.L. 94 1/16" flammability rating was V-1.

Examples XXXIII-XXXX

In substantial accordance with the procedures described in Examples IX and XXXI, poly(brominated phenylene oxide) compositions of varying molecular weights were prepared and incorporated into Shell 335 high impact polystyrene; these styrene compositions contained 15 percent (by weight of total composition) of flame retardant, 3 percent (by weight of total composition) of antimony trioxide, and 6 percent (by weight of total composition) of Solprene 411P. Samples of the high impact polystyrene compositions obtained were prepared and tested for flammability with the U.L. test. The results of this experiment are shown below in Table IV wherein the molecular weight of each flame retardant as well as the U.L. 94 1/16" flammability rating and the average number of seconds it took the samples tested to self extinguish after the igniting flame was removed from them is indicated.

TABLE IV

| EXAMPLE NUMBER | V.P.O. MOLECULAR WEIGHT | $M_n$ | $M_w$ | U.L. 94 1/16" RATING |
| --- | --- | --- | --- | --- |
| XXXIII | >10,000 | 7395 | 12340 | V-1 (7.2 seconds) |
| XXXIV | >10,000 | 4287 | 9387 | V-1 (4.3 seconds) |
| XXXV | 7390 | 4328 | 9480 | V-1 (5.8 seconds) |
| XXXVI | 4670 | 3832 | 8125 | V-0 (2.2 seconds) |
| XXXVII | 3855 | 3302 | 4460 | V-0 (1.4 seconds) |
| XXXVIII | 3200 | 3189 | 5733 | V-0 (2.2 seconds) |
| XXIX | 2480 | 2837 | 5327 | V-0 (0.8 seconds) |
| XXXX | 1875 | 2833 | 4028 | V-0 (0.7 seconds) |

Examples XXXXI and XXXXII

In substantial accordance with the procedures described in Examples IX and XXXI, poly(brominated phenylene oxide) compositions of high molecular weight were prepared and incorporated into Shell 35 high impact polystyrene; these compositions contained 15 percent (by weight of total composition) of flame retardant, 3 percent (by weight of total composition) of antimony trioxide, and 6 percent (by weight of total composition) of Solprene 411P.

The flame retardant additive used in Example XXXXI had a molecular weight in excess of 10,000 and a softening point range of from about 225 to about 240 degrees centigrade; it was soluble in both tetrahydrofuran (at 25 degrees centigrade) and chloroform (at 25 degrees centigrade). The flame retardant additive used in Example XXXXII had a molecular weight in excess of 10,000 and a softening point range of from about 245 to about 290 degrees centigrade; it was insoluble in both tetrahydrofuran (at 25 degrees centigrade) and chloroform (at 25 degrees centigrade).

Injection molded samples of the polystyrene compositions of these Examples were prepared for testing and evaluated.

The polystyrene composition of Example XXXXI had a U.L. 94 1/16" rating of V-1 (7.2 seconds). The Izod impact of the test specimen was 1.35 foot-pounds per inch.

The polystyrene composition of Example XXXXII had a U.L. 94 1/16" rating of V-1 (6.7 seconds). The Izod impact of the test specimen was 0.86 foot-pounds per inch.

Example XXXXIII

In substantial accordance with the procedure described in Example IX, poly(brominated phenylene oxides) were prepared from 2,4,6-tribromophenol; the molecular weight of this composition (as determined by the vapor phase osmometry method described in test ASTM D2503-67) was about 3830. The number average molecular weight (as determined by the gel permeation chromatography method described in this specification) was about 3302.

In substantial accordance with the procedure described in Example XXIV, high impact polystyrene compositions containing 15 percent (by weight of total composition) of the poly(brominated phenylene oxide) described in the first paragraph of this Example, 3 percent (by weight of total composition) of antimony trioxide, and 6 percent (by weight of total composition) of Solprene 411P were prepared; injection molded samples were prepared for testing.

One sample was subjected to accelerated aging by being exposed to a temperature of 150 degrees Fahrenheit for 48 hours; the other sample, the control, was not subjected to these conditions.

The surface area for the top and bottom surfaces of each of the samples was measured; for each sample, the combined surface area for the top and bottom surfaces was about 5.89 square inches.

The control sample and the sample subjected to accelerated aging conditions were each wiped with separate pieces of filter paper. The filter paper used was then subjected to spectrometric analysis with the General Electric XRD 5 Fluorescence Spectrometer. The analytical procedure used was essentially the same as the procedure described in a paper entitled "The Determination of Sulfur, Lead, and Silicon in Atmospheric Aerosols—An Application of X-ray Fluorescence and Confined Spot Paper Techniques"; this paper, which was prepared by J. L. Johnson, A. C. Ottolini, F. A.

Forster, and R. B. Loranger and was published by the Research Laboratories of General Motors Corporation as "Research Publication GMR-1128" on or about October of 1972 and was presented at the ANACHEMS Conference held in Dearborn, Mich. in October of 1972.

No surface bromine (in the form of poly[brominated phenylene oxide]) was detected in the control sample.

No surface bromine (in the form of poly[brominated phenylene oxide]) was detected in the sample which had been subjected to a temperature of 150 degrees Fahrenheit for 48 hours.

Examples XXXXIV to XXXXIX

High impact polystyrene plastic compositions were prepared by incorporating either Noryl ® (a composition containing poly[2,6-dimethyl-1,4-phenylene ether] which is available from the General Electric Company) and/or flame retardant prepared in accordance with the procedure of Example IX and/or antimony trioxide into "Cosden Polystyrene 825 TVP1", a high impact polystyrene available from the Cosden Oil and Chemical Company; in the Table accompanying these Examples, the former composition is referred to as "poly(phenylene oxide)" and the latter composition is referred to as "poly(brominated phenylene oxide)".

Two control polystyrene plastic compositions were prepared. The first of these contained only Cosden Polystyrene 825 TVP1; the second contained 6 percent (by weight) of antimony trioxide and 94 percent (by weight) of Cosden Polystyrene 825 TVP1.

The additives were admixed with the polystyrene by addition to a Brabender Prep Center Mixer ("Measuring Head", Model R6, C. W. Brabender Instruments, Inc., South Hackensack, N.J.); the mixer was equipped with a pair of roller-type blades positioned with a head provided with heat transfer means. The resultant mixtures were heated to a temperature of 205 degrees centigrade; at this temperature they were in a molten state. Each formulation was discharged from the mixer, cooled, and ground into chips. The chips were injection molded in a one-ounce Newbury Injection Molder (Model HI-30 RS, Newbury Industries, Inc., Newbury, Ohio); a 60 second molding cycle with a ram pressure of 2000 p.s.i. was utilized, and these chips were subjected to heat, melted, and then injected into a mold in order to provide solid samples for testing.

The samples so prepared were tested for flammability in accordance with the Underwriters' Laboratory Subject No. 94 test referred to in Example IX.

The results obtained in these tests are shown in Table V. In each case the samples tested contained only Cosden Polystyrene 825 TVP1 and the specified amount(s) of antimony trioxide and/or poly(phenylene oxide) and/or poly(brominated phenylene oxide). The concentrations of these additives are indicated as a weight-percent, and they were calculated as a function of the combined weights of the polystyrene, antimony trioxide, and phenylene oxide polymers which were used in each Example.

TABLE V

| EXAMPLE NUMBER | PERCENT (BY WEIGHT) OF COSDEN POLYSTYRENE 825 TVP1 IN SAMPLE | PERCENT (BY WEIGHT) OF POLY(PHENYLENE OXIDE) IN SAMPLE | PERCENT (BY WEIGHT) OF POLY(BROMINATED PHENYLENE OXIDE) IN SAMPLE | PERCENT (BY WEIGHT) OF ANTIMONY TRIOXIDE IN SAMPLE | U.L. RATING (⅛" SAMPLE) |
|---|---|---|---|---|---|
| XXXXIV | 100 | 0 | 0 | 0 | HB |
| XXXXV | 94 | 0 | 0 | 6 | HB |
| XXXXVI | 70 | 30 | 0 | 0 | HB |
| XXXXVII | 67 | 30 | 0 | 3 | HB |
| XXXXVIII | 70 | 0 | 30 | 0 | HB |
| XXXXIX | 82 | 0 | 15 | 3 | V-0 |

As previously indicated, it is most preferred that the flame retardant condensation product of this invention is derived from tribromophenol. It has been found that the condensation product of tribromophenol in accordance with the present invention has a novel molecular structure exhibiting desirable properties over closely related compositions.

More specifically, the preferred flame retarding condensation product of this invention is a branched polymer having a hydroxyl number of from 2.8 to about 30 and the structural formula

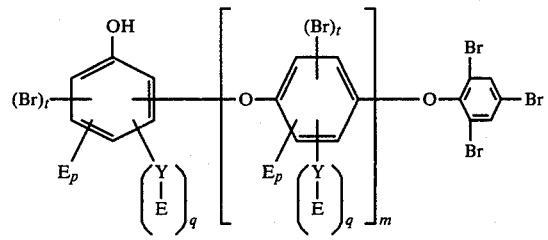

wherein each repeating unit set out within the brackets of the structural formula is attached in an ortho or para configuration to its adjacent phenyl and phenoxy moiety; and wherein E is an end group of the formula

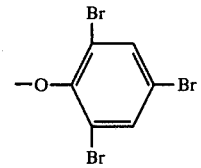

Y is a side chain of the same structure and configuration as said repeating unit; the substituents Br, E and Y on each phenyl ring are attached only to the ortho or para positions relative the hydroxyl group in the structural formula and the oxygen atom in the repeating unit; each t, p and q are independently the integer 0 or 1, provided that the sum of t plus p plus q equals 2, and provided that from about 10 to about 80 percent of the repeating units have the side chain and end unit —Y—E attached thereto; and m is an integer such that the total molecular weight of the polymer ranges from about 2,000 to about 20,000.

The novelty and unexpected desired properties of the polymer described above are attributed to both the chemical as well as its structural configuration. First the polymer, because it is a condensation product of a phenol, necessarily has a residual hydroxyl group. This group can be titrated and accordingly the polymer has a hydroxyl number dependent on its molecular weight. As stated, this hydroxyl number typically ranges from 2.8 to about 30 mg per gram of sample.

It has also been found that the condensation of tribromophenol as described herein results in a 1-2 and 1-4 substitution of bromine relative the phenolic moiety. Therefore, each repeating phenoxy group in the polymer is attached to an ortho or para position relative the phenolic group on the adjacent ring. Thus, any two repeating units have the following structural configuration.

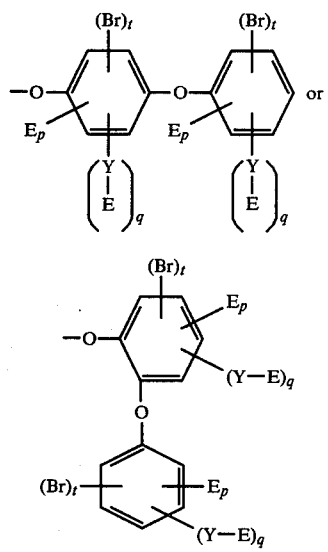

wherein Y, E, t, p and q are as heretofore described. Similarly, the side chains represented by Y and the end groups represented by E are attached to the ortho or para position of the respective phenoxy ring.

An important aspect of the preferred fire retardant condensation product is its branching i.e. the existence of side groups on otherwise linear polymer backbone. These side groups can be one or more repeating units as in the backbone of the polymer terminated by an end group or simply an end group by itself. The degree of branching in the preferred product can vary such that at least one in ten of the phenoxy units are substituted by a side chain or end group and as many as eight in 10 are so substituted. It is believed that this degree of branching significantly contributes to the non-blooming properties of polyester compositions containing the preferred product.

The preferred condensation product of the present invention has a number average molecular weight that ranges from about 2000 to about 20,000, and most preferably from about 2000 to about 12,000 as determined by vapor phase osmometry (VPO).

The preferred condensation product of tribromophenol of the present invention can be prepared by the general procedure heretofore described. A further more specific exemplary preparation is set forth in the following example.

Example XIII

Sodium tribromophenate (387 grams) dissolved in water to obtain a 37 percent by weight solution is charged into a reaction vessel equipped with stirring and heating means. Hydrochloric acid (1.9 grams; 31.5% concentration) is added and the resulting mixture is warmed to 40° C. with stirring. Potassium persulfate (2.3 grams) is added to the reaction vessel and stirring is continued for a period of about 30 minutes. A reaction temperature of 55° to 60° C. is maintained during this period. After this time the pH of the reaction mixture is adjusted to about 13 by the addition of 50% aqueous caustic soda and thereafter hydrazine (1 gram; 64% conc.) is added with stirring. Stirring is continued for a period of 15 minutes and the reaction mixture is thereafter heated to a temperature of 95° to 100° C. with further stirring for a period of 4 hours. After this time the mixture is cooled to room temperature and the desired product is recovered by filtration and dried.

I claim:

1. A flame retarded polystyrene composition comprising from about 50 to about 90 parts by weight polystyrene, from about 9 to about 22 parts by weight of a branched polymer having a hydroxyl number of from 2.8 to about 30 of the structural formula

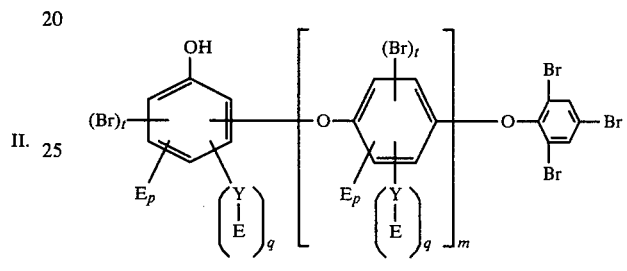

wherein each repeating unit set out within the brackets of the structural formula is attached in an ortho or para configuration to its adjacent phenyl and phenoxy moiety; and wherein E is an end group of the formula

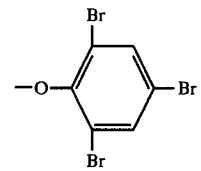

Y is a side chain of the same structure and configuration as said repeating unit; the substituents Br, E and Y on each phenyl ring are attached only to the ortho or para positions relative the hydroxyl group in the structural formula and the oxygen atom in the repeating unit; each t, p and q are independently the integer 0 or 1, provided that the sum of t plus q plus q equals 2, and provided that from about 10 to about 80 percent of the repeating units have the side chain and end unit —Y—E attached thereto; and m is an integer such that the total molecular weight of the polymer ranges from 2000 to 20,000, and from about 1 to about 10 parts by weight fire retarding enhancing agent comprising an oxide or chloride of antimony, arsenic, bismuth, tin, lead or germanium.

2. The flame retarded polystyrene composition of claim 1, wherein the branched polymer has a molecular weight of from 2000 to 12,000.

3. The flame retarded polystyrene composition of claim 1, wherein the fire retarding enhancing agent is an oxide of antimony, arsenic or bismuth.

4. The flame retarded polystyrene composition of claim 1, wherein the fire retarding enhancing agent is antimony trioxide.

5. The flame retarded polystyrene composition of claim 1, wherein the polystyrene is high impact polystyrene.

* * * * *

UNITED STATES PATENT AND TRADEMARK OFFICE
CERTIFICATE OF CORRECTION

PATENT NO. : 4,353,820

DATED : October 12, 1982

INVENTOR(S) : Michael W. Lindvay

It is certified that error appears in the above-identified patent and that said Letters Patent are hereby corrected as shown below:

Col. 1, line 19, "extended" should be --extruded--.

Col. 1, line 60, "the" should be --them--.

Col. 4, line 33, "compositions" should be --composition--.

Col. 5, line 13, "exygen bonded" should be --oxygen atom bonded--.

Col. 5, line 57, "stell" should be --steel--.

Col. 8, line 65, "in toto" should be --*in toto*--.

Col. 13, line 2, "411P" should be --411P.--.

Col. 13, line 24, "Examples" should be --Example--.

Col. 13, line 29, "foot pounds" should be --foot-pounds--.

Col. 17, line 13, "tion." should be --tion--.

Signed and Sealed this

Fifth Day of April 1983

[SEAL]

Attest:

GERALD J. MOSSINGHOFF

Attesting Officer    Commissioner of Patents and Trademarks